United States Patent [19]  
Krass et al.

[11] Patent Number: 4,464,533  
[45] Date of Patent: Aug. 7, 1984

[54] HERBICIDALLY ACTIVE QUINOLINE OR QUINOXALINE BENZOATE DERIVATIVES

[75] Inventors: Dennis K. Krass, Canal Fulton; Sidney B. Richter, Fairlawn, both of Ohio

[73] Assignee: PPG Industries, Inc., Pittsburgh, Pa.

[21] Appl. No.: 440,053

[22] Filed: Nov. 8, 1982

[51] Int. Cl.³ .................. C07D 241/44; C07D 215/22; A01N 43/60; A01N 43/38
[52] U.S. Cl. .................................... 544/354; 546/157; 71/88; 71/92
[58] Field of Search ........................................ 544/354

[56] References Cited

FOREIGN PATENT DOCUMENTS 42750 12/1980 European Pat. Off. .
23785 3/1981 European Pat. Off. .
46467 3/1982 European Pat. Off. .
46468 3/1983 European Pat. Off. .

OTHER PUBLICATIONS

Derwent Abstract 27353 (E/14), 26/02/82 of Japan 70-35574.

Primary Examiner—Mark L. Berch  
Attorney, Agent, or Firm—Edward J. Whitfield

[57] ABSTRACT

Disclosed are certain herbicidally active quinoline or quinoxaline benzoate derivatives, herbicidal compositions containing these compounds and the use of such compounds to control the growth of noxious plants, i.e., weeds.

4 Claims, No Drawings

HERBICIDALLY ACTIVE QUINOLINE OR QUINOXALINE BENZOATE DERIVATIVES

DESCRIPTION OF THE INVENTION

This invention relates to certain quinoline or quinoxaline benzoate derivatives of the Formula I:

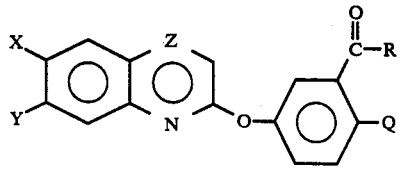

wherein,

Q is a halogen (e.g., chlorine, bromine or fluorine), nitro, or cyano;

X and Y are the same or different and represent hydrogen, halogen (e.g., chlorine, bromine or fluorine), alkyl or haloalkyl (e.g., trifluoromethyl) of up to 4 carbon atoms;

Z is nitrogen or —CH—; and

R is —OH, —OM, —OR$^1$, —SR$^1$ or —NR$^2$R$^3$ wherein M is an agronomically suitable salt (e.g., sodium, potassium or ammonium);

R$^1$ is C$_1$ to C$_{12}$ alkyl optionally monosubstituted by hydroxy or C$_1$ to C$_{12}$ alkoxy, —R$^4$COOR$^5$, wherein R$^4$ is C$_1$ to C$_3$ alkylene optionally monosubstituted by C$_1$ to C$_4$ alkyl and R$^5$ is hydrogen, C$_1$ to C$_{10}$ alkyl or an agronomically suitable salt;

R$^2$ is hydrogen, C$_1$ to C$_{12}$ alkyl or C$_3$ to C$_{12}$ alkenyl;

R$^3$ is hydrogen C$_1$ to C$_{12}$ alkyl, C$_3$ to C$_{12}$ alkenyl, C$_1$ to C$_6$ alkoxy, C$_2$ to C$_6$ alkylcarbomyl or C$_1$ to C$_6$ alkane sulfonyl.

Preferred compounds of the Formula I are those wherein at least one of X and Y is halogen, e.g., chlorine, or trifluoromethyl, Z is nitrogen, Q is nitro, and R is —OR$^1$ wherein R$^1$ is —R$^4$COOR$^5$.

Compounds of this invention embodied in the Formula I are believed to be herbicidally active and would be effective in regulating growth of a wide variety of undesirable plants, i.e., weeds, when applied, in herbicidally effective amount, to the growth medium prior to emergence of the weeds or to the weeds subsequent to emergence from the growth medium. The term "herbicidally effective amount" is that amount of compounds or mixture of compounds of this inventin required to so injure or damage weeds such that the weeds are incapable of recovering following application. The quantity of compound or mixture of compounds of this invention applied in order to exhibit a satisfactory herbicidal effect may vary over a wide range and depends on a variety of factors, such as, for example, hardiness of a particular weed species, extent of weed infestation, climatic conditions, soil conditions, method of application and the like. Typically, as little as one or less pound per acre of compound or mixture of compounds of this invention would be expected to provide satisfactory weed control, although in some instances application rates in excess of one pound per acre, e.g., up to 5 pounds per acre might be required. Of course, the efficacy of a particular compound against a particular weed species may readily be determined by routine laboratory or field testing in a manner well known to the art.

A compound or compounds of this invention may, of course, be used as such or in formulation with agronomically acceptable adjuvants, inert carriers, other herbicides, or other commonly used agricultural compounds, for example, insecticides, fungicides, stabilizers, safeners, fertilizers or the like. The compounds of this invention alone or in formulation with other agronomically used materials are typically applied in the form of dusts, granules, wettable powders, solutions, suspensions, aerosols, emulsions, dispersions or the like in a manner well known to the art. When formulated with other typically used agronomically acceptable materials, the amount of compound or compounds of this invention may vary over a wide range, for example, from about 0.05 to 95 percent by weight on weight of formulation. Typically, such formulations would contain from about 5 to 75 percent by weight of compound or compounds of this invention.

A compound or compounds of this invention are effective in controlling a variety of common broad-leaved and grassy weeds at application rates of only a few grams per acre either pre- or postemergent. Exemplary of weeds that may be effectively controlled by the application of compounds of this invention are barnyard grass (*Echinochloa crusgalli*), crabgrass (*Igitaria sauguinalis*), coffeeweed (*Daubentonia punices*), jimsonweed (*Datura stamonium*), johnsongrass (*Sorghum halepense*), tall morningglory (*Ipomoea purpurea*), wild mustard (*Brassica caber*), teaweed (*Sida Spinosa*), velvetleaf (*Abutilin Theophrasti*), wild oat (*Avena fatua*), yellow foxtail (*Setaria glauca*), yellow nutsedge (*Cyperus esculentus*) and the like.

The Formula I compounds of this invention may be prepared by reacting the alkali metal, e.g., potassium salt, of appropriately substituted hydroxyquinoline or hydroxyquinoxaline of the Formula II:

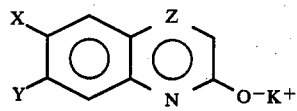

wherein X, Y and Z are as previously defined with the alkali metal, e.g., potassium salt, of a fluorinated, substituted benzoic acid of the Formula III:

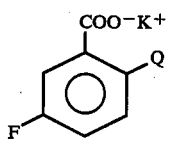

wherein Q is as previously defined, to form a benzoic acid compound of the Formula IV:

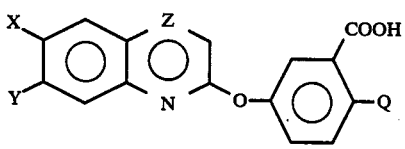

The Formula IV compound is then reacted with an α-halo compound, e.g., an α-halocarboxylate of the Formula V:

wherein:

Hal is halogen, e.g., bromine or chlorine; and
R⁴ and R⁵ are as previously defined, to form an invention compound of the Formula I.

The foregoing mode of synthesis is illustrated more specifically as follows:

(a) A reactor is charged with 4.34 grams (0.02 mole) of the potassium salt of 6-chloro-2-hydroxyquinoline (Formula II Compound) in 25 milliliters of dimethylsulfoxide. To this mixture is added 4.46 grams (0.02 mole) of the potassium salt of 5-fluoro-2-nitrobenzoate (Formula III Compound). After stirring at about 100° C. for about 16 hours, the reaction mixture is poured into 200 milliliters of water and acidified with concentrated hydrochloric acid. Filtration and air drying affords 5-(6-chloro-2-quinolinoxy)-2-nitrobenzoic acid (Formula IV Compound).

(b) A reactor, provided with a reflux condenser, is charged with 6.88 grams (0.01 mole) of 5-(6-chloro-2-quinolinoxy)-2-nitrobenzoic acid, prepared as described in part (a), dissolved in 55 milliliters of benzene. To this solution is added 3.0 grams (0.022 mole) of ethyl 2-chloropropionate (Formula V Compound) and 3.34 grams (0.02 mole) of 1,8-diazabicyclo[5.4.0]undec-7-ene (DBU). After 6 hours at reflux, the reaction mixture is cooled, filtered and the filtrate washed with 0.25 normal sodium hydroxide solution and saturated aqueous sodium chloride solution and dried over anhydrous magnesium sulfate. Filtration and removal of solvent affords the desired 1-[1-(ethoxycarbonyl)ethyl] 5-(6-chloro-2-quinolinoxy)-2-nitrobenzoate.

The manner of preparing a specific compound within the scope of this invention is described in some detail by the foregoing, and it is to be understood that other Formula I compounds can be prepared in like manner by simply varying the choice of starting materials. The compounds of this invention may also be prepared by alternative methods. For example, the compound 1-[1-(ethoxycarbonyl)ethyl] 5-(6-chloro-2-quinolinoxy)-2-nitrobenzoate prepared as described hereinabove, may also be prepared as follows:

Substantially equimolar amounts of 2,6-dichloroquinoline and the potassium salt of 3-hydroxybenzoic acid are reacted, in an inert organic solvent, e.g., dimethylsulfoxide giving 5-(6-chloro-2-quinolinoxy)benzoic acid which is nitrated, with, for example, potassium nitrate in the presence of concentrated sulfuric acid to give the corresponding 2-nitrobenzoic acid. The 2-nitrobenzoic acid is then reacted with a suitably substituted—halo compound, e.g., 2-chloropropionate, as described hereinabove.

Although the invention has been described in some detail with reference to certain embodiments thereof, it is to be understood that it is not intended to be so limited, since many variations may be made therein by those skilled in the art without departing from the spirit and scope thereof as defined in the appended claims.

We claim:

1. A compound of the formula:

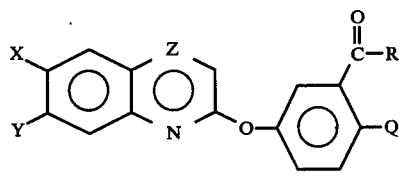

wherein:

Q is halogen, nitro, or cyano;

X and Y are the same or different and represent hydrogen, halogen, alkyl or haloalkyl of up to 4 carbon atoms;

Z is nitrogen; and

R is —OH, —OM, —OR¹, —SR¹ or —NR²R³ wherein M is an agronomically suitable salt (e.g., sodium, potassium or ammonium);

R¹ is $C_1$ to $C_{12}$ alkyl optionally monosubstituted by hydroxy or $C_1$ to $C_{12}$ alkoxy, —R⁴COOR⁵, wherein R⁴ is $C_1$ to $C_3$ alkylene optionally monosubstituted by $C_1$ to $C_4$ alkyl and R⁵ is hydrogen, $C_1$ to $C_{10}$ alkyl or an agronomically suitable salt;

R₂ is hydrogen, $C_1$ to $C_{12}$ alkyl or $C_3$ to $C_{12}$ alkenyl;

R₃ is hydrogen $C_1$ to $C_{12}$ alkyl, $C_3$ to $C_{12}$ alkenyl, $C_1$ to $C_6$ alkoxy, $C_2$ to $C_6$ alkyl carbonyl or $C_1$ to $C_6$ alkane sulfonyl.

2. A compound of claim 1 wherein at least one of X and Y is halogen or trifluoromethyl.

3. A compound of claim 1 wherein R is —OR¹ and R¹ is —R⁴COOR⁵.

4. A compound of claim 1 wherein Q is nitro.

* * * * *